(12) United States Patent  
Feuerlein et al.

(10) Patent No.: US 8,687,763 B2  
(45) Date of Patent: Apr. 1, 2014

(54) METHOD AND DEVICE TO DETERMINE THE VALUE OF AN X-RAY TUBE VOLTAGE

(75) Inventors: Ute Feuerlein, Erlangen (DE); Sebastian Gehrsitz, Himmelstadt (DE); Christiane Koch, Eggolsheim (DE); Rainer Raupach, Heroldsbach (DE)

(73) Assignee: Siemens Aktiengesellschaft, Munich (DE)

(*) Notice: Subject to any disclaimer, the term of this patent is extended or adjusted under 35 U.S.C. 154(b) by 312 days.

(21) Appl. No.: 13/293,366

(22) Filed: Nov. 10, 2011

(65) Prior Publication Data

US 2012/0140893 A1    Jun. 7, 2012

(30) Foreign Application Priority Data

Nov. 10, 2010  (DE) .......................... 10 2010 043 709

(51) Int. Cl.  
*H05G 1/30* (2006.01)

(52) U.S. Cl.  
USPC ........................................... 378/16; 378/110

(58) Field of Classification Search  
USPC .................... 378/16, 109, 110, 8, 97, 108  
See application file for complete search history.

(56) References Cited

U.S. PATENT DOCUMENTS 7,970,097 B2 * 6/2011 Bruder et al. ..................... 378/8  
2007/0258559 A1 * 11/2007 Hur ................................ 378/16

OTHER PUBLICATIONS

"Radiation Dose and Image Quality in Pediatric CT: Effect of Technical Factors and Phantom Size and Shape," Siegel et al. Radiology, vol. 233 (2004 pp. 515-522.  
"Automatic Selection of tube Potential for Radiation Dose Reductions in CT: A General Strategy," Yu et al., Med. Phys., vol. 37, No. 1 (2010) pp. 234-242.

* cited by examiner

*Primary Examiner* — Hoon Song  
(74) *Attorney, Agent, or Firm* — Schiff Hardin LLP (57) ABSTRACT

The value of a tube voltage of an x-ray tube, used to acquire x-ray projections of a patient in order to generate at least one image in each phase of a multiphase examination, is determined from a contrast-to-noise ratio that establishes the desired image quality of the image in each phase, and the tube current for each tube voltage for each phase is determined given a constantly maintained contrast-to-noise ratio for different tube voltages. For each phase, a value for the dose of x-ray radiation is defined for each different tube voltage and the associated determined tube current. From among the different tube voltages, a tube voltage is set that causes the total dose of x-ray radiation applied to the patient to be as low as possible for all phases of the examination.

17 Claims, 3 Drawing Sheets

METHOD AND DEVICE TO DETERMINE THE VALUE OF AN X-RAY TUBE VOLTAGE

BACKGROUND OF THE INVENTION

1. Field of the Invention

The invention concerns a method to determine the value of a tube voltage of an x-ray tube of an x-ray device in order to acquire x-ray projections in a multiphase examination of a defined tissue to be examined of a patient, in order to generate at least one image of the defined tissue to be examined in each phase of the multiphase examination. The invention also concerns an x-ray device (in particular a computed tomography apparatus) which is designed to execute such a method. The invention also concerns a non-transitory, computer-readable data storage medium encoded with programming instructions that enable a processor or computer, in which the storage medium is loaded, to execute a method of the type described above.

2. Description of the Prior Art

In medical technology, given imaging with x-ray radiation, for example in computed tomography (CT), it is always sought to apply an optimally low dose of x-ray radiation to a patient to generate one or more images of a tissue of the patient. However, a defined image quality must also be achieved in order to be able to answer the clinical question at issue using the generated image or images, which requires a minimum dose. Relevant measures of image quality are the image noise or the image contrast, for example. In particular, the image contrast of defined elements and materials (such as iodine used as a contrast agent in computed tomography) has a relatively strong dependency on the spectrum of the x-ray radiation that is used. Given the use of relatively low tube voltages, the spectrum of the x-ray radiation is such that the image contrast of iodine increases. Inasmuch, given the use of iodine the dose of x-ray radiation that is applied to a patient to achieve an optimally high image quality also depends on the spectrum of the x-ray radiation.

In CT angiograms to show blood-carrying vessels—in which the visibility of iodine is practically of exclusive importance—the dose of x-ray radiation applied to a patient is therefore reduced by the use of relatively low tube voltages (see also M. J. Siegel et al., "Radiation Dose and Image Quality in Pediatric CT: Effect of Technical Factors and Phantom Size and Shape", Radiology 2004; 233: Page 515 to 522).

In "Automatic selection of tube potential for radiation dose reduction in CT: A general strategy", L. Yu et al. propose a method to select a tube voltage suitable for a specific examination with regard to a reduction of the dose of x-ray radiation that is to be applied to a patient, in which method an iodine contrast-to-noise ratio is used as an image quality index in connection with a noise constraint parameter α in order to be able to characterize and account for the different requirements for the image quality for different examinations. Different noise constraint parameters α are available for adaptation for different examinations. With the noise constraint parameter it should be achieved that the absolute image noise does not exceed a certain value. For a CT angiogram in which the iodine contrast-to-noise ratio is practically of exclusive relevance, the noise constraint parameter α is selected between 1.5 and 2.0. The noise constraint parameter α is selected between 1.1 and 1.25 for breast, torso or pelvic examinations with contrast agent, and α is selected equal to one for breast, torso or pelvic examinations without contrast agent. The tube voltage with which the lowest dose of x-ray radiation is applied to the patient for a specific examination is determined based on a "relative dose factor" (RDF) into which the contrast-to-noise ratio of iodine and the noise constraint parameter α enter.

A particular problem results in a multiphase examination of a specific tissue—the liver, for example—of which at least one image is respectively generated in different phases or in different states in order to be able to differentiate different types of lesions in the liver from one another for diagnostic purposes. In the case of the liver, the different phases or states are produced by the administration of contrast agent which is taken up at different temporal rates by the lesions of different types. The multiphase examination of the liver therefore includes what is known as a native scan of the liver without contrast agent as a first phase of the examination, a scan of the liver after the administration of a contrast agent in a second arterial phase of the liver, and a scan of the liver after the administration of a contrast agent in a third venous phase of the liver, in which scans respective images of the liver are generated. In order to be able to assess the time variation of the absorption of contrast agent by the lesions of different types, it is necessary for a significant acquisition parameter of the x-ray device (such as the tube voltage) to coincide or be the same in all scans, i.e. in all acquisitions of x-ray projections. However, this requirement is generally not compatible with the fact that the minimum dose of x-ray radiation should be applied to the patient in each scan while maintaining a high image quality. This is due to the fact that the liver is different during the native scan and the two scans with contrast agent whose concentration is different in the arterial phase and venous phase of the liver, and the fact that the image quality required by the user can be different in the different phases. Therefore different optimal tube voltages for the three phases can result with regard to the lowest dose of x-ray radiation to be applied to the patient in each scan, in particular with the necessary adherence to or compliance with the technical limits of the x-ray device with regard to the ability to adjust acquisition parameters (such as the tube voltage, the tube current, etc.).

SUMMARY OF THE INVENTION

An object of the invention is to provide a method, an x-ray device, a computed program and an encoded data storage medium to determine the value of a tube voltage for a multiphase examination such that the dose of x-ray radiation that is applied to the patient in total is as low as possible in all phases of the multiphase examination given adjustment of the value of the tube voltage during the acquisition of x-ray projections of said patient.

The invention is based on the insight to provide, for each phase of a multiphase examination of a defined tissue to be examined of a patient, a contrast-to-noise ratio establishing the desired image quality of at least one image to be generated for that phase, and to determine the respective associated tube current for different potential tube voltages that can be suitably set given a constantly maintained contrast-to-noise ratio, thus given an essentially constant image quality, and, together with an associated, determined tube current, to define for each potentially suitable tube voltage a value $D_{ij}$ with $i \in [1, 2, \ldots, x]$ a tube voltage in question $j \in [I, II, \ldots, y]$ a phase of the multiphase examination for the dose of x-ray radiation to be applied to the patient given this parameter configuration for the acquisition of x-ray projections.

In this manner parameter configurations including the tube voltage, the associated tube current and a dose value $D_{ij}$ are present for the different phases of the multiphase examination. Using these parameter configurations, the tube voltage can be selected for a defined tissue that causes the total dose of x-ray radiation applied to the patient in all phases of the multiphase examination during the acquisition of x-ray projections of the patient to be optimally low, complying with the technical adjustment capability of the associated acquisition parameters at the x-ray device. A total dose value $$D_i = D_{iI} + D_{iII} + \ldots + D_{iy}$$

with $i \in [1, 2, \ldots, x]$ a tube voltage in question is thus essentially determined for all tube voltages in question, and ultimately the tube voltage whose total dose value is lowest or as low as possible, is selected while allowing for the technical adjustment capability of the associated acquisition parameters at the x-ray device. In this way, not only is an optimally low dose of x-ray radiation applied to the patient for the acquisition of the x-ray projections of the multiphase examination, but also the requirements to generate qualitatively high-grade images of the defined tissue to be examined in each phase are satisfied by the contrast-to-noise ratio being kept constant for each phase.

In an embodiment of the invention, for each phase, a reference tube voltage and a reference tube current and/or a reference noise of the image of the defined tissue to be examined of the patient that is to be generated from x-ray projections acquired for a phase, are provided to establish the contrast-to-noise ratio that is to be provided and held constant for each phase. The reference tube voltage and the reference tube current represent reference values for the respective desired image quality that establish a defined noise level for images of the defined tissue to be examined that are to be generated. Additionally or alternatively, a reference noise can be directly provided in the form of a reference noise level for the image noise. Assistance in the specification of a reference tube voltage and a reference tube current and the specification of a reference noise level can be provided by the x-ray device presenting, at a user interface of the x-ray device, suggested values for selection based on experimental values, after specification by the user of the defined tissue to be examined.

According to a further embodiment of the invention, for each phase the determination of the tube current belonging to each potentially suitable tube voltage, given a constantly maintained contrast-to-noise ratio, takes place based on the dependency (different in each phase) of the contrast of the defined tissue to be examined on the value of the tube voltage of the x-ray tube, and based on the dependency (different in each phase) of the noise of images of the defined tissue to be examined that are to be generated on the value of the tube voltage and the tube current of the x-ray tube.

In application to a multiphase examination of the liver, this means that the contrast of liver tissue without contrast agent (iodine), the contrast of liver tissue containing contrast agent in the arterial phase and the contrast of liver tissue containing contrast agent in the venous phase, each have a different dependency on the tube voltage, and thus on the spectrum of the x-ray radiation, due to the different concentration of iodine in the liver tissue in each phase. The same applies to the noise. If the contrast-to-noise ratio (provided by means of a reference tube voltage and a reference tube current and/or a reference noise level) is kept constant for each phase, the associated tube current can respectively be determined based on the known dependencies for all suitable tube voltages that can potentially be set.

According to an embodiment of the invention, for different tissue of patients that are to be examined—for example for liver tissue, heart tissue etc.—the dependency (which is different in each phase of a multiphase examination of that tissue) of the contrast of the tissue to be examined on the value of the tube voltage of the x-ray tube for each phase is stored in a data memory from which the respective dependency of the contrast can be extracted for the respective phase.

The different (in each phase of a multiphase examination) dependency of the contrast of the different tissues to be examined on the spectrum of the x-ray radiation or on the value of the tube voltage of an x-ray tube has been determined in advance by means of simulations or by means of calibration measurements (for example using appropriately prepared phantoms) and is kept available for retrieval in the data memory or a database.

According to one embodiment of the invention, the multiphase examination of the defined tissue to be examined is provided manually to the x-ray device or is obtained from an electronic patient record (that designates the defined tissue to be examined) of the patient of a hospital or radiology information system. Since the defined tissue to be examined is thus known, the dependencies (different in each phase of a multiphase examination of that tissue) of the contrast of the defined tissue to be examined on the spectrum of the x-ray radiation, and thus on the value of the tube voltage of the x-ray tube, can be learned from the data memory.

According to another embodiment of the invention, the specification of the dependency (different in each phase of the multiphase examination) of the contrast of the defined tissue to be examined on the value of the tube voltage of the x-ray tube is based on the fact that the spectral dependency of a tissue can be represented as a linear combination of the known spectral dependencies on two other known chemical elements or materials, with the selection of the phase of the defined tissue to be examined taking place (with setting means) between the two known other chemical elements or materials. The setting means can be a slide control (slider) and a scale representing examination types, tissues and/or phases of tissues. The parameterization of the respective tissue contrast is thereby mapped to a one-dimensional problem in the form of the adjustment of a slider, which can be realized in a graphical user interface, for example.

According to another embodiment of the invention, the first chemical element is water and the second chemical element is iodine. Positions between the end positions of water or iodine represent mixtures of water and iodine with different proportions with which the contrast of a defined tissue can be respectively associated at defined points according to the scale.

According to a further embodiment of the invention, for different tissues of patients that are to be examined the dependency (different in each phase of the multiphase examination) of the noise of images generated from the defined tissue to be examined on the value of the tube voltage and the tube current of the x-ray tube for each phase is stored in a data memory, from which data memory the respective dependency of the noise for the respective phase is extracted. The respective dependency (different in each phase of the multiphase examination of a tissue) of the noise on the value of the tube voltage and the tube current for the defined tissue to be examined can again have been determined in advance via computer simulations or via calibration measurements, for example using appropriately prepared phantoms.

According to a further embodiment of the invention, the CTDI ("Computed Tomography Dose Index") value and/or the DLP ("Dose Length Product") value are determined as a value for the dose of x-ray radiation that is to be applied to the patient. In computed tomography the CTDI value indicates the dose in milligrays (mGy) that is applied to a patient in an acquisition slice. If the CTDI value is multiplied with the length of the examination volume, the DLP value is obtained, i.e. the dose of x-ray radiation that is applied to a patient in the course of a scan.

In a development of the invention, for each phase a conflict value is determined that indicates whether the acquisition of the x-ray projections of a defined tissue of the patient that is to be examined can be implemented with the additional acquisition parameters within the system limits of the x-ray device, which conflict value is determined for each potentially suitable tube voltage with regard to the additional acquisition parameters of the x-ray device—for example the tube current etc.—that are to be set that belong to the respective potentially suitable tube voltage. Each configuration of acquisition parameters is thus checked for its ability to be set at the x-ray device or, respectively, its technical permissibility for the x-ray device. For each parameter configuration a conflict value $K_{ij}$ therefore exists with $i \in [1, 2, \ldots, x]$ a tube voltage in question $j \in [I, II, \ldots, y]$ a phase of the multiphase examination, which conflict value $K_{ij}$ can in principle be freely defined. For example, a scale from zero to ten could be established for the conflict value, wherein the value zero could indicate "no conflict" (thus that implementation is possible without any problems) and the value ten could indicate "highest conflict" or, respectively, impossible. The parameter configurations can be classified in this manner.

According to another embodiment of the invention, a global conflict value $K_i$ is determined that indicates whether the acquisition of the x-ray projections of the defined tissue of the patient that is to be examined can be implemented with the additional acquisition parameters within the system its of the x-ray device in each phase of the multiphase examination, which global conflict value $K_i$ is determined for each potentially suitable tube voltage to be set at the x-ray tube, based on the conflict values $K_{ij}$ determined for the respective tube voltage for each phase.

For each global conflict value $K_i$ the maximum loss of image quality that is to be expected is indicated ($K_i$: max$\{K_{iI}, K_{iII}, \ldots, K_{ij}\}$).

According to a further embodiment of the invention, from the suitable tube voltages that can potentially be set that one tube voltage is ultimately selected that has a global conflict value $K_i$ according to which the acquisition of the x-ray projections of the defined tissue of the patient that is to be examined can be implemented with the additional acquisition parameters within the known system limits of the x-ray device, without conflict or with the least global conflict value. If the multiphase examination should be implementable with a small global conflict value, the acquisition parameters causing the conflict or conflicts would be limited to just the values that are allowable within the system limits.

The above object also is achieved in accordance with the present invention by a non-transitory, computer-readable data storage medium encoded with programming instructions that, when the data storage medium is loaded into a computerized control device for an x-ray imaging system, cause the control device to operate the x-ray imaging system in accordance with one or more embodiments of the method described above.

DESCRIPTION OF THE PREFERRED EMBODIMENTS

Figure 1:
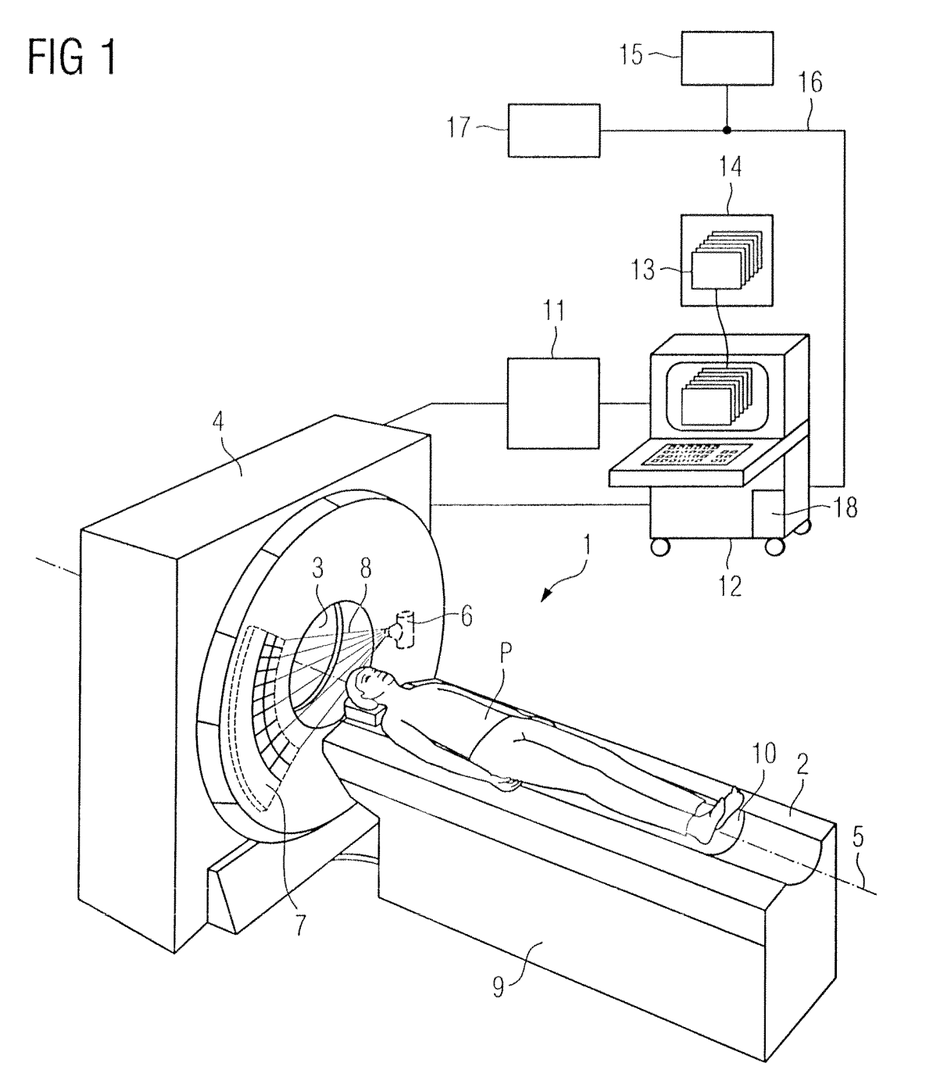
FIG. 1 schematically illustrates a computed tomography apparatus with which the invention can be implemented.

A computed tomography apparatus 1 that is suitable to execute the method according to the invention is shown in FIG. 1. The computed tomography apparatus 1 has a patient bed 2 to support a patient P to be examined. The computed tomography apparatus 1 also has a gantry 4 with a tube/detector system mounted such that it can rotate around a system axis 5. The tube/detector system has an x-ray tube 6 and an x-ray detector unit 7 situated opposite one another. In operation, x-ray radiation 8 emanates from the x-ray tube 6 in the direction of the x-ray detector unit 7 and is detected by the detector unit 7.

The patient bed 2 has a bed base 9 on which is arranged a patient support plate 10 that actually supports the patient P. The patient support plate 10 is adjustable relative to the bed base 9 such that the patient bearing plate 10 with the patient P can be introduced into the opening 3 of the gantry 4 to acquire x-ray projections of the patient P, for example for a topogram or in a spiral scan. The computational processing of the x-ray projections—for example the generation of a topogram, a slice image or the reconstruction of a volume data set of a body region or, respectively, a tissue of the patient P based on the x-ray projections—takes place with an image computer 11 (schematically shown) of the computed tomography apparatus 1.

The computed tomography apparatus 1 moreover has a computer 12 with which computer programs for operation and control of the computed tomography apparatus 1 are executed. The computer 12 does not need to be fashioned as a separate computer 12; rather, it can also be integrated into the computed tomography apparatus 1.

In the exemplary embodiment of the invention, a multiphase examination of a defined tissue (presently the liver tissue) of the patient P is to be implemented with the computed tomography apparatus 1. In the exemplary embodiment of the invention, the multiphase examination of the liver tissue includes three phases or three scans in which the liver tissue respectively exhibits different states or a different composition due to the administration of a contrast agent in the form of iodine. The first scan is known as a native scan of the liver or of the liver tissue without the presence of iodine in the liver tissue, which represents the first phase I of the examination. The second scan of the liver tissue subsequently takes place after the administration of iodine as a contrast agent in a second, arterial phase II of the liver tissue with a relatively high concentration of iodine in the liver tissue. The third scan of the liver tissue takes place in a third, venous phase III of the liver in which the concentration of iodine in the liver tissue is relatively low. As already mentioned, different types of lesions that are present in liver tissue take up the iodine at different rates, such that the different types of lesions can be diagnosed on the basis of slice images generated from x-ray projections taken of the liver tissue respectively in the three phases.

As used herein a scan means the acquisition of x-ray projections of the liver tissue from different directions with the x-ray detector system. A multiphase examination is the generation of images—in the exemplary embodiment of the invention, the generation of slice images of the liver tissue of the patient P for the three phases of the examination—whose evaluation forms the basis of the clinical diagnosis or the answer to a clinical question. For the generation of the slice images for the three phases, an optimally low total dose of x-ray radiation should be applied to the patient P while maintaining an image quality that is necessary or desired for the clinical diagnosis or for the solution to the clinical question.

For this purpose, the computer 12 is provided with a computer program 13 with which the value of that tube voltage of the x-ray tube 6 can be determined given whose setting and given whose use the dose of x-ray radiation applied in total to the patient P is as low as possible during the acquisition of the x-ray projections of the body region of the patient P that comprises the liver for or in all phases of the multiphase examination. The computer program 13 thereby realizes the method described in the following to determine the aforementioned tube voltage, which method can have been loaded into the computer 12 from a portable memory medium (for example from a CD 14 or a memory stick) or from a server 15 (as a data medium) via a network 16.

Via a graphical user interface (not shown) of the computer 12, a user can enter the examination type, thus a multiphase examination of liver tissue as the defined tissue to be examined. The choice or selection of a multiphase examination of liver tissue can also take place based on an electronic hospital or patient record of the patient P that, for example, can be retrieved via the network 16 from an HIS 17 (Hospital Information System) or RIS 17 (Radiology Information System) and from which the multiphase examination of liver tissue is to be learned.

Since the multiphase examination of liver tissue is known in this manner, the data about the dependency (different in each phase of the multiphase examination) of the image contrast of liver tissue on the spectrum of the x-ray radiation or on the tube voltage can be learned from a data memory 18 of the computer 12. Since the tube voltage is causative of the spectrum of x-ray radiation, only the tube voltage is discussed in the following.

Figure 2:
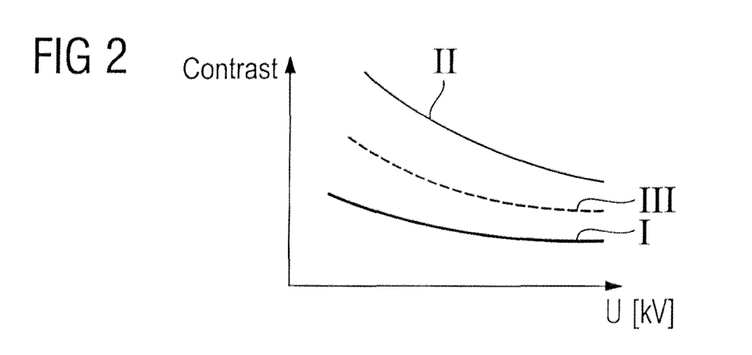
FIG. 2 through 8 are diagrams for explaining the method according to the invention.

The dependency of the image contrast of liver tissue on the tube voltage U for the three phases I, II and III of the multiphase examination (as can be learned from the data memory 18) is schematically illustrated in the diagram of FIG. 2. The image contrast of only liver tissue is practically of exclusive relevance in the native phase I. The image contrast of iodine in the liver tissue is practically of exclusive relevance in the second, arterial phase II with a high concentration of iodine in the liver tissue. In the third, venous phase III with lower concentration of iodine in the liver tissue, the dependency of the image contrast with respect to the tube voltage lies between that of the first phase and the second phase. However, the data for the phases I through III do not necessarily need to exist as a diagram; rather, they can also be stored for retrieval in the data memory 18 as a table or in another suitable form.

Furthermore, the dependency of the image noise on the tube voltage U and the tube current (which dependency is different for each phase I through III of the phase examination) is stored for retrieval in the data memory 18 for the three phases I through III of the liver tissue. In the case of the present exemplary embodiment of the invention, the dependency of the noise on the tube voltage has respectively been determined in the form of a curve progression for liver tissue for each phase of the different tube currents, meaning that a tube current belonging to a defined noise level and a defined tube voltage can be determined for each phase from the curve progressions. These data can also be stored for retrieval in the data memory 18 in table form or in another suitable manner.

The correlations between image contrast and tube voltage as well as between image noise, tube voltage and tube current that are comprised in the data memory 18 have been determined in advance for different phases of different tissue by means of computer simulations or calibration measurements, for example using phantoms correspondingly prepared for the respective tissue.

Alternatively, the parameterization of the image contrast of the liver tissue for the three phases I through III can also be produced with a slider of the graphical user interface, with which slider a scale is associated that comprises examination types, tissues and/or phases of tissues. Use is made of the fact that the spectral dependency of a tissue or material can generally be represented as a linear combination of the known spectral dependencies on two known, different chemical elements or materials. This is possible because the absorption of x-ray radiation is essentially always determined by the photoelectric effect and the Compton effect. Water (which forms the first end of the scale) and iodine (which forms the second end of the scale) suggest themselves as characteristic materials or, respectively, chemical elements. Positions between the end positions of water or iodine represent mixtures of water and iodine with different proportions with which the contrast of a defined tissue or a defined tissue composition can respectively be associated at defined points according to the scale.

In a further preparation of the multiphase examination of the liver tissue of the patient P, in the case of the present exemplary embodiment of the invention a topogram of the body region of the patient P that comprises the liver is acquired with the computed tomography apparatus 1 in a known manner.

The scan protocol for the native scan of the liver tissue normally already includes a suggestion for the tube voltage and the tube current that are to be set for the scan of the liver tissue. Using the topogram, the user can leave these or adapt them as necessary with regard to the desired image quality for the slice images of the liver tissue that are to be generated. In this way a reference protocol with a reference tube voltage and a reference tube current is provided by the user. Alternatively or additionally, a reference value for the level of allowable image noise for the slice images to be generated can also be provided by the user as an image quality parameter.

Figure 3:
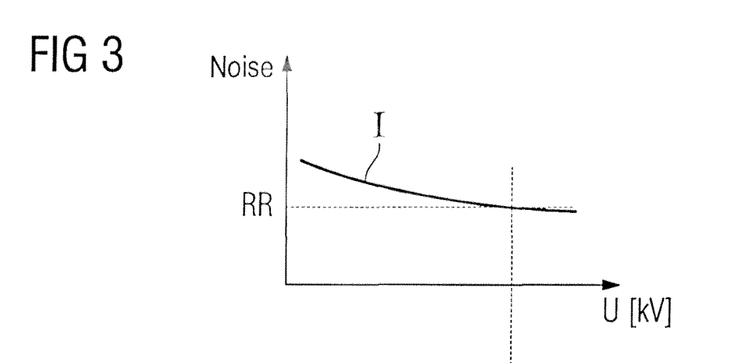
Figure 4:
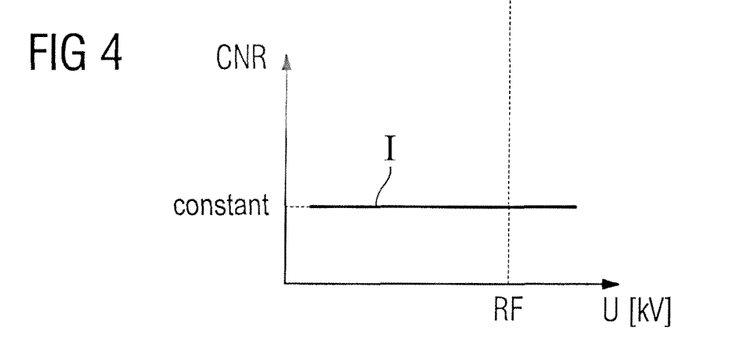

To further determine the tube voltage, the contrast-to-noise ratio for the liver tissue is held constant under consideration of the reference tube voltage and the reference tube current and/or the reference value of the image noise. The reference tube voltage and the reference tube current and/or the reference value of the image noise thus establish the contrast-to-noise ratio to be held constant as an image quality feature for invariant image quality given varying tube voltage. In FIG. 3 the reference tube voltage RF and the reference noise level RR are plotted as examples for the native phase I. The constantly maintained contrast-to-noise ratio CNR for the native phase I, based on the reference tube voltage RF and the reference noise level RR, is illustrated in FIG. 4. FIG. 3 shows the dependency of the noise on the tube voltage for the constantly maintained contrast-to-noise ratio CNR, which dependency was determined for the constantly maintained contrast-to-noise ratio CNR for the native phase I from the aforementioned dependency of the noise on the tube voltage and the dependency of the contrast on the tube voltage for the native phase I that were determined for different tube currents. The progressions for the phases II and III, i.e. for the tissue compositions belonging to the phases II and III, qualitatively correspond to the progression shown in FIG. 3.

For each of the possible tube voltages of the x-ray tube 6 that are considered for the native scan of the liver tissue, the associated tube current is finally, respectively determined given a constantly maintained contrast-to-noise ratio for the liver tissue. Depending on how the image contrast and the image noise for the liver tissue change given different tube voltages, a different tube current results so that the contrast-to-noise ratio is constant as was predetermined.

Figure 5:
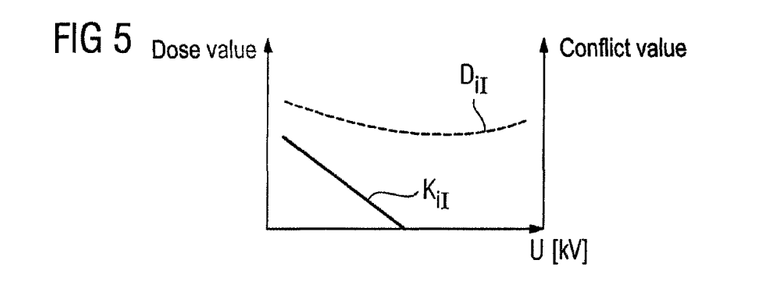

If the tube currents belonging to the different potential tube voltages in question are determined for the native phase, for each potential tube voltage that can be set at least one value for the dose $D_{iI}$ of x-ray radiation to be applied to the patient (with i∈[1, 2, ..., x]) is respectively determined under consideration of the respectively determined tube current. In the exemplary embodiment of the invention, for each possible tube voltage in question, the CTDI value (the computed tomography dose index) is determined as a dose value and the DLP value or dose length product is determined. The latter results from the CTDI value multiplied with the length of the examination volume. In FIG. 5 the DLP values belonging to the potential tube voltages U in question are plotted over the tube voltage for the native phase I.

For the arterial phase II and the venous phase III, the DLP values belonging to the potential tube voltages U in question are determined in a corresponding manner, meaning that, for the arterial phase II and the venous phase III as well, the contrast-to-noise ratio for the liver tissue is held constant given variation of the tube voltage, respectively starting from a reference tube voltage and a reference tube current and/or a reference value of the image noise, and the DLP values are determined based on the tube currents belonging to the various tube voltages.

Figure 6:
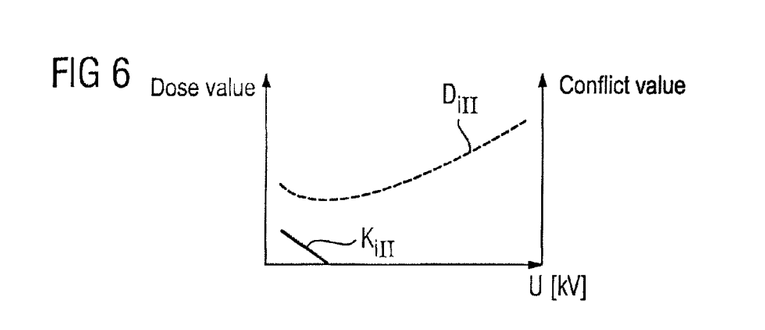
Figure 7:
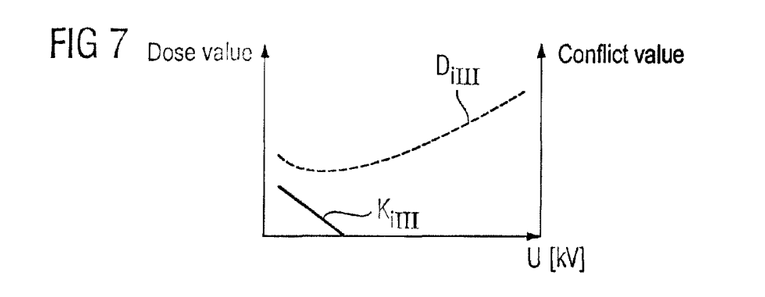

FIG. 6 shows the progression of the dose values $D_{iII}$ with i∈[1, 2, ..., x] over the tube voltage for the arterial phase II. In a corresponding manner, FIG. 7 shows the progression of the dose values $D_{iIII}$ with i∈[1, 2, ..., x] over the tube voltage for the venous phase III.

For each tube voltage in question, a sum dose value $$D_i = D_{iI} + D_{iII} + D_{iIII}$$

with
i∈[1, 2, x] a tube voltage in question
is subsequently determined. Furthermore, based on this an order of the potential tube voltages in question for the multiphase examination is created, wherein the order begins with the tube voltage with which the lowest sum dose value is associated, Since additional acquisition parameters such as the tube current etc. belong to each tube voltage in each phase, it must additionally be checked with which potentially suitable tube voltage (together with additional associated acquisition parameters) the scan with the computed tomography apparatus can even be implemented within the system limits of said computed tomography apparatus 1.

In the exemplary embodiment of the invention, for each phase I through III a conflict value $K_{ij}$ (that indicates whether the acquisition of the x-ray projections of the liver tissue can be implemented within the system limits of the computed tomography apparatus 1 with the additional acquisition parameters) is therefore determined for each potential tube voltage in question and its associated additional acquisition parameters. For example, it must be checked whether the tube current belonging to a potential tube voltage in question exceeds the maximum allowable tube current at the system, or whether the maximum allowable tube load for the duration of the scan is exceeded. If an overrun occurs for a parameter configuration, in the case of the present exemplary embodiment of the invention a conflict value between zero and ten is assigned depending on the scale of the overrun, wherein the value zero means "no conflict", thus that implementation can occur without any problems, and the value ten means "highest conflict" or unfeasible.

The conflict values $K_{iI}$ i∈[1, 2, ..., x] that are determined for the native scan or, respectively, the first phase I are additionally plotted in FIG. 5 for a tube voltage in question. From FIG. 5 it is apparent that no conflict occurs at higher tube voltages since the conflict values $K_{iI}$ are "zero". In a corresponding manner, the conflict values $K_{iII}$ i∈[1, 2, ..., x] for a tube voltage in question are plotted in FIG. 6 for the arterial or second phase II, and the conflict values $K_{iIII}$ i∈[1, 2, ..., x] for a tube voltage in question are plotted in FIG. 7 for the venous or third phase III.

A global conflict value $$K_i = K_{iI} + K_{iII} + K_{iIII}$$

is determined for each potential tube voltage in question, based on the determined conflict values $K_{ij}$, which global conflict value indicates whether the acquisition of the x-ray projections of the liver tissue of the patient can be implemented with the additional acquisition parameters, within the system limits of the x-ray device, in each phase of the multiphase examination.

The maximum loss of image quality that is to be expected is advantageously indicated for each global conflict value $K_i$ ($K_i$: max{$K_{iI}, K_{iII}, ..., K_{ij}$}).

Finally, from the potentially suitable tube voltages that can be set, that tube voltage is determined or, respectively, selected that has a global conflict value $K_i$ according to which the acquisition of the x-ray projections of the liver tissue of the patient P can be implemented without conflict (or possibly with the lowest global conflict value) in each phase I through III, within the known system limits of the x-ray device, with the additional acquisition parameters, and for which tube voltage the associated total dose value is lowest. If the multiphase examination should be implementable with only a small global conflict value, the acquisition parameter or parameters causing the conflict would be limited to just the values that are permissible within the system limits.

Figure 8:
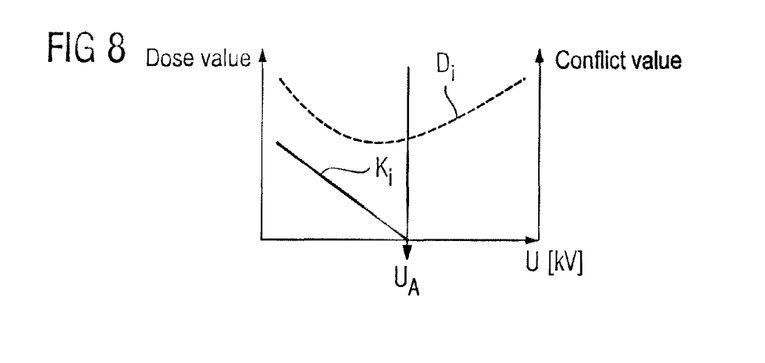

FIG. 8 illustrates the final determination or, respectively, selection of the tube voltage to be set for the case of the present exemplary embodiment of the invention. In FIG. 8 the total dose values $D_i$ and the global conflict values $K_i$ are plotted over the tube voltage U. According to FIG. 8, that tube voltage $U_A$ is selected that is suitable without conflict given the lowest total dose to acquire the x-ray projections in the three phases.

However, the selection of the tube voltage can also primarily be oriented towards the lowest total dose value even if a global conflict value is associated with this, as long as the three scans can possibly be implemented with limitation of individual acquisition parameters, for example with limitation of the maximum tube current.

If the tube voltage is determined, the multiphase examination is or, respectively, the scans are implemented with the tube voltage.

The invention was described in the preceding in an example of liver tissue, but the method according to the invention is not limited to liver tissue and can also be implemented for any other tissue.

Although modifications and changes may be suggested by those skilled in the art, it is the intention of the inventors to embody within the patent warranted hereon all changes and modifications as reasonably and properly come within the scope of their contribution to the art.

We claim as our invention:
1. A method for operating an x-ray imaging system, said x-ray imaging system comprising an x-ray tube operated with a tube voltage and a tube current associated with said tube voltage, and a computerized control unit, said method comprising:

from said computerized control unit, operating said x-ray imaging system to acquire x-ray projections in a multiphase examination of defined tissue of a patient to generate, in each phase of said multiphase examination, at least one image of said defined tissue;

for each phase in said multiphase examination, providing a contrast-to-noise ratio to said computerized control unit that establishes a desired image quality of said at least one image to be generated in that phase;

in said computerized control unit, determining a tube current for each tube voltage, among different potential tube voltages, that maintains said contrast-to-noise ratio constant in that phase;

for each phase, determining in said computerized control unit a dose of x-ray radiation to be applied to the patient for each of said potential tube voltages and the determined tube current associated therewith; and from said computerized control unit, for each phase of said multiphase examination, setting a value of said tube voltage of said x-ray tube, from among said different potential tube voltages that causes a total dose of x-ray radiation applied to the patient for all of the phases of said multiphase examination to be as low as possible during acquisition of said x-ray projections.

2. A method as claimed in claim 1 comprising, for each phase, predetermining at least one of a reference tube voltage and a reference tube current or a reference noise in said at least one image of said defined tissue generated in that phase, that establishes the contrast-to-noise ratio that is to be maintained constant in that phase.

3. A method as claimed in claim 1 comprising, in each phase, determining, in said computerized control unit, a tube current for each potential tube voltage, that maintains said contrast-to-noise ratio constant in that phase, based on a dependency, that is different in each phase, of a contrast of said defined tissue on a value of the tube voltage and, based on a dependency, that is different in each phase, of a noise in said at least one image of said defined tissue in that phase on a value of the tube voltage and a value of the tube current.

4. A method as claimed in claim 3 comprising storing in a memory a plurality of different dependencies, that are different in each phase of said multiphase examination, respectively for different defined tissues, of the contrast of each defined tissue on said value of the tube voltage, and accessing said data memory from said computerized control unit to acquire the respective dependencies, different in each phase of said multiphase examination, for the defined tissue to be examined.

5. A method as claimed in claim 3 comprising setting, via a setting element of said computerized control unit, a specification of said dependency, that is different in each phase of said multiphase examination, of the contrast of said defined tissue on the value of the tube voltage, as a selected linear combination of known spectral dependencies of two known, different chemical elements or materials.

6. A method as claimed in claim 5 comprising setting said specification using a slider as said setting element that comprises a scale having opposite scale ends respectively representing different examination types, different tissues or different phases of tissues.

7. A method as claimed in claim 5 wherein a first of said two known, different chemical elements or materials is water and a second of said two known, different chemical elements or materials is iodine.

8. A method as claimed in claim 3 comprising storing, in a data memory, for each of a plurality of different defined tissues to be examined, a dependency, that is different in each phase of said multiphase examination, of said noise of said at least one image on the value of the tube voltage and the value of the tube current, and accessing said data memory from said computerized control unit to retrieve said dependency, in each phase, for the defined tissue to be examined.

9. A method as claimed in claim 1 comprising manually entering, into said computerized control unit, a designation of the defined tissue to be examined in said multiphase examination.

10. A method as claimed in claim 1 comprising, from said computerized control unit, accessing an electronic patient record of a hospital or radiology information system, that includes a designation of the defined tissue to be examined in said multiphase examination to determine, in said computerized control unit, the defined tissue that is to be examined in said multiphase examination.

11. A method as claimed in claim 1 comprising determining, in said computerized control unit, a value for said dose of said x-ray radiation to be applied to the patient as at least one of a computed tomography dose index (CTDI) and a dose length product (DLP).

12. A method as claimed in claim 1 comprising, in said computerized control unit, determining, for each phase in said multiphase examination, a conflict value for each potential tube voltage with respect to additional parameters of said x-ray device associated with each potential tube voltage, said conflict value indicating whether acquisition of said x-ray projections of said defined tissue can be implemented with said additional acquisition parameters within system limits of said x-ray device.

13. A method as claimed in claim 12 comprising, in said computerized control unit, determining, from the conflict values respectively determined for each phase for the respective potential tube voltages, a global conflict value for each potential tube voltage that indicates whether acquisition of the x-ray projections of said defined tissue can be implemented in each phase of said multiphase examination with said additional acquisition parameters within said system limits of the x-ray device.

14. A method as claimed in claim 13 comprising, in said computerized control unit, for each global conflict value, specifying a maximum loss of image quality.

15. A method as claimed in claim 13 comprising, from among the potential tube voltages, selecting a tube voltage having a global conflict value that allows said x-ray projections of the defined tissue to be acquired with said additional acquisition parameters in each phase within said system limits of the x-ray device without conflict or with a smallest global conflict value.

16. An x-ray imaging system comprising:
an x-ray tube operated with a tube voltage and a tube current associated with said tube voltage;
a computerized control unit;
said computerized control unit being configured to operate said x-ray tube to acquire x-ray projections in a multiphase examination of defined tissue of a patient to generate, in each phase of said multiphase examination, at least one image of said defined tissue;
said computerized control unit being provided, for each phase in said multiphase examination, with a contrast-to-noise ratio that establishes a desired image quality of said at least one image to be generated in that phase;
said computerized control unit being configured to determine a tube current for each tube voltage, among different potential tube voltages, that maintains said contrast-to-noise ratio constant in that phase;

said computerized control unit being configured to determine, for each phase, a dose of x-ray radiation to be applied to the patient for each of said potential tube voltages and the determined tube current associated therewith; and said computerized control unit being configured to set, for each phase of said multiphase examination, a value of said tube voltage of said x-ray tube, from among said different potential tube voltages that causes a total dose of x-ray radiation applied to the patient for all of the phases of said multiphase examination to be as low as possible during acquisition of said x-ray projections.

17. A non-transitory, computer-readable data storage medium encoded with programming instructions that is loadable into a computerized control unit of an x-ray imaging system comprising an x-ray tube operable with a tube voltage and an associated tube current, said programming instructions causing said computerized control unit to:

operate said x-ray imaging system to acquire x-ray projections in a multiphase examination of defined tissue of a patient to generate, in each phase of said multiphase examination, at least one image of said defined tissue;

receive as an input, for each phase in said multiphase examination, a contrast-to-noise ratio to said computerized control unit that establishes a desired image quality of said at least one image to be generated in that phase;

determine a tube current for each tube voltage, among different potential tube voltages, that maintains said contrast-to-noise ratio constant in that phase;

for each phase, determine in said computerized control unit a dose of x-ray radiation to be applied to the patient for each of said potential tube voltages and the determined tube current associated therewith; and set, for each phase of said multiphase examination, a value of said tube voltage of said x-ray tube, from among said different potential tube voltages that causes a total dose of x-ray radiation applied to the patient for all of the phases of said multiphase examination to be as low as possible during acquisition of said x-ray projections.

* * * * *